United States Patent [19]
Wong

[11] Patent Number: 5,103,096
[45] Date of Patent: * Apr. 7, 1992

[54] RAPID FIRE DETECTOR

[75] Inventor: Jacob Y. Wong, Santa Barbara, Calif.

[73] Assignee: Gaztech Corporation, Goleta, Calif.

[*] Notice: The portion of the term of this patent subsequent to Jun. 25, 2008 has been disclaimed.

[21] Appl. No.: 503,215

[22] Filed: Apr. 2, 1990

Related U.S. Application Data

[63] Continuation-in-part of Ser. No. 403,587, Sep. 6, 1989, Pat. No. 5,026,992.

[51] Int. Cl.⁵ .............................................. G01N 21/61
[52] U.S. Cl. .................................... 250/343; 250/339; 250/352
[58] Field of Search ................ 250/339, 343, 352, 346

[56] References Cited

U.S. PATENT DOCUMENTS

| | | | |
|---|---|---|---|
| 4,177,381 | 12/1979 | McClatchie et al. | 250/343 |
| 4,499,379 | 2/1985 | Miyatake et al. | 250/343 |
| 4,501,068 | 2/1985 | Ebi et al. | 250/343 |
| 4,647,777 | 3/1987 | Meyer | 250/339 |

FOREIGN PATENT DOCUMENTS

62-105033  5/1987  Japan .................................. 250/343

Primary Examiner—Constantine Hannaher
Attorney, Agent, or Firm—Daniel C. McKown

[57] ABSTRACT

A compact low-cost fire detector responds quickly by detecting an increase in the concentration of carbon dioxide gas in the ambient air. The detector also calculates the rate of build-up of carbon dioxide. The detector avoids the use of moving parts by employing a differential temperature black body source of infrared radiation in conjunction with a dual pass band filter. One of the pass bands is located at the 4.26 micron absorption band of carbon dioxide gas and the other pass band is located at 2.20 microns at which none of the atmospheric gases has an absorption band. The latter channel serves as a reference and renders the detector immune to false alarms caused by dust or smoke particles in the air or due to deterioration of certain components. The fire detector makes use of a sample chamber that consists of a serpentine passage in a block of material, the walls of the serpentine passsage being highly reflective so as to act as a light pipe.

26 Claims, 3 Drawing Sheets

RAPID FIRE DETECTOR

RELATED PATENT APPLICATIONS

This application is a continuation-in-part of U.S. Pat. Application Ser. No. 07/403,587 filed Sept. 6, 1989 by Jacob Y. Wong for "Spectral Ratioing Technique for NDIR Gas Analysis Using a Differential Temperature Source, now U.S. Pat. No. 5,026,992. The priority date of Sept. 6, 1989 is claimed for material common to that application and the present application. The earlier application in its entirety is incorporated herein by reference.

In that earlier application, the present inventor disclosed an instrument using a differential temperature source and a dual pass band filter to determine the concentration of a gas in a sample chamber. Methane was used as an exemplary gas. The possibility of using that type of instrument as a fire sensor by detecting an elevated level of carbon dioxide was mentioned, but was not elaborated on.

That possibility became a reality with the invention, by the present inventor, of a novel sample chamber uniquely suited for use in a fire detector. That sample chamber is disclosed in a U.S. Patent Application, filed on even date herewith, and titled "Gas Sample Cell."

BACKGROUND OF THE INVENTION

1. Field of the Invention

The present invention is in the field of early warning devices for fire detection and more particularly relates to a compact apparatus which measures the concentration and the rate of change in the concentration of carbon dioxide at the onset of a fire as a means for its early and rapid detection.

2. The Prior Art

The fire detectors that are available commercially today fall into three basic classifications, namely flame sensing, thermal and smoke detectors. This classification is designed to respond to the three principal types of energy and matter characteristics of a fire environment: flame, heat and smoke.

The flame sensing detector is designed to respond to the optical radiant energy generated by the diffusion flame combustion process—the illumination intensity and the frequency of flame modulation. Two types of flame detectors are commonly in use: the ultraviolet (UV) detectors which operate beyond the visible at wavelengths below 4,000A, and the infrared detectors which operate in the wavelengths above 7,000 A. To prevent false signals from the many sources of ultraviolet and infrared optical radiation present in most hazard areas the detectors are programmed to respond only to radiation with frequency modulation within the flicker frequency range for flame (5-30 Hz).

Flame detectors generally work well and seldom generate false alarms However, they are relatively complex and expensive fire detectors which are not amenable to low-cost and mass-oriented usage. Instead they are mostly utilized in specialized high-value and unique protection areas such as aircraft flight simulators, aircraft hangars, nuclear reactor control rooms, etc.

Thermal detectors are designed to operate from thermal energy output—the heat—of a fire. This heat is dissipated throughout the area by laminar and turbulent convection flow. The latter is induced and regulated by the fire plume thermal column effect of rising heated air and gases above the fire surface. There are two basic types of thermal detectors: the fixed temperature type and the rate of rise detector type. The fixed temperature type further divides into the spot type and the line type. The spot detector involves a relatively small fixed unit with a heat-responsive element contained within the unit or spot location of the detector. With the line detector the thermal reactive element is located along a line consisting of thermal-sensitive wiring or tubing. Line detectors can cover a greater portion of the hazard area than can spot detectors.

Fixed temperature thermal fire detectors rate high on reliability, stability and maintainability but low on sensitivity. In modern buildings with high air flow ventilation and air conditioning systems, placing the fixed temperature detector is a difficult engineering problem. Consequently, this type of thermal fire detector is not widely used outside of very specialized applications.

A rate of rise detector type thermal fire detector is usually installed where a relatively fast-burning fire is expected. The detector operates when the fire plume raises the air temperature within a chamber at a rate above a certain threshold of operation—usually 15° F. per minute. However, if a fire develops very slowly and the rate of temperature rise never exceeds the detector's threshold for operation, the detector may not sense the fire.

The newest type of thermal fire detector is called a rate compensated detector which is sensitive to the rate of temperature rise as well as to a fixed temperature level which is designed into the detector's temperature rating. Even with this dual approach, the most critical problem for effective operation of thermal fire detectors is the proper placement of detectors relative to the hazard area and the occupancy environment. Consequently, this type of fire detector is seldom found in everyday households.

By far the most popular fire detector in use in everyday life today is the smoke detector. Smoke detectors respond to the visible and invisible products of combustion. Visible products of combustion consist primarily of unconsumed carbon and carbon-rich particles; invisible products of combustion consist of solid particles smaller than approximately five (5) microns, various gases, and ions. All smoke detectors can be classified into two basic types: photoelectric type which responds to visible products of combustion and ionization type which responds to both visible and invisible products of combustion.

The photoelectric type is further divided into 1) projected beam and 2) reflected beam. The projected beam type of smoke detectors generally consist of a series of sampling piping from the holds or other protected space on the ship to the photoelectric detector. The air sample is drawn into the piping system by an electric exhaust pump. The photoelectric detector is usually enclosed in a metal tube with the light source mounted at one end and the photoelectric cell at the other end. This type of detector is rather effective due to the length of the light beam. When visible smoke is drawn into the tube, the light intensity of the beam received in the photoelectric cell is reduced because it is obscured by the smoke particles. The reduced level of light intensity causes an unbalanced condition in the electrical circuit to the photocell which activates the alarm. The projected beam or smoke obscuration detector is one of the most established types of smoke detectors. In addition to use on ships, these detectors are commonly used to protect high-value compartments or other storage areas, and to provide smoke detection for plenum areas and air ducts.

The reflected light beam smoke detector has the advantage of a very short light beam length, making it adaptable to incorporation in the spot type smoke detector. The projected beam smoke detector discussed earlier becomes more sensitive as the length of the light beam increases, and often a light beam of 5 or 10 feet long is required. However, the reflected light beam type of photoelectric smoke detector is designed to operate with a light beam only 2 or 3 inches in length. A reflected beam visible light smoke detector consists of a light source, a photoelectric cell mounted at right angles to the light source, and a light catcher mounted opposite to the light source.

Ionization type smoke detectors detect both the visible and invisible particle matter generated by the diffusion flame combustion. As indicated previously, visible particulate matter ranges from 4 to 5 microns in size, although smaller particles can be seen as a haze when present in a high mass density. The ionization detector operates most effectively on particles from 1.0 to 0.01 microns in size. There are two basic types of ionization detectors. The first type has a bipolar ionized sampling chamber which is the area formed between two electrodes. A radioactive alpha particle source is also located in this area. The oxygen and nitrogen molecules of air in the chamber are ionized by alpha particles from the radioactive source. The ionized pairs move towards the electrodes of the opposite sign when electrical voltage is applied, and a minute electrical current flow is established across the sampling chamber. When combustion particles enter the chamber they attach themselves to the ions. Since the combustion particles have a greater mass, the mobility of the ions now decreases, leading to a reduction of electrical current flow across the sampling chamber. This reduction in electrical current flow initiates the detector alarm.

The second type of ionization smoke detector has a unipolar ionized sampling chamber instead of a bipolar one. The only difference between the two types is the location of the area inside the sampling chamber that is exposed to the alpha source. In the case of the bipolar type the entire chamber is exposed leading to both positive and negative ions (hence the name bipolar). In the case of the unipolar type only the immediate area adjacent the positive electrode (anode) is exposed to the alpha source. This results in only one predominant type of ions (negative ions) in the electrical current flow between the electrodes (hence the name unipolar).

Although unipolar and bipolar sampling chambers use different principles of detector design they both operate by the combustion products creating a reduced current flow and thus activating the detector. In general the unipolar design is superior in giving the ionization smoke detectors a greater level of sensitivity and stability, with fewer fluctuations of current flow to cause false signals from variations in temperature, pressure and humidity. Most ionization smoke detectors available commercially today are of the unipolar type.

For the past two decades the ionization smoke detectors have dominated the fire detector market. One of the reasons is that the other two classes of fire detectors, namely the flame sensing detectors and the thermal detectors are appreciably more complex and costlier than the ionization smoke detectors. They are therefore mainly used only in specialized high-value and unique protection areas. In recent years, because of their relatively high cost, even the photoelectric smoke detectors have fallen behind significantly in sales to the ionization type. The ionization type are generally less expensive, easier to use and can operate for a full year with just one 9-volt battery. Today over 90 percent of households that are equipped with fire detectors use the ionization type smoke detectors.

Despite their low cost, relatively maintenance-free operation and wide acceptance by the buying public, the smoke detectors are not without problems and certainly far from being ideal. There are a number of significant drawbacks for the ionization smoke detectors to operate successfully as early warning fire detectors. To state it plainly most people do not complain about them simply because there are no better alternatives.

One of the biggest problems with ionization smoke detectors is their frequent false-alarms. By the nature of its operational principle, any micron-size particulate matters other than the smoke from an actual fire can set off the alarm. Kitchen grease particles generated by a hot stove is one classic example. Over-zealous dusting of objects and/or furniture near the detector is another. Frequent false-alarms are not just a harmless nuisance; some people actually disarm their smoke detectors by temporarily removing the battery in order to escape from such annoying episodes. This latter situation could be outright dangerous especially when these people forget to rearm their smoke detectors.

Another significant drawback for the current ionization smoke detector is its relatively slow speed to alert people of a fire. There are several factors that contribute to this particular drawback. The first fact is the detector trigger threshold for smoke which directly affects its response time to the onset of a fire. No doubt a lower trigger threshold would mean a faster fire detector. However, it also means more frequent annoying false alarms for the user. The second factor is the particular placement of the detector with respect to the spot where fire breaks out. Unlike ordinary gases, smoke is actually a complex sooty molecular cluster that consists mostly of carbon. It is much heavier than air and thus diffuses much slower than the gases we encounter everyday. Therefore, if the detector happens to be at some distance from the location of the fire, it will be a while before enough smoke gets into the sampling chamber of the smoke detector to trigger the alarm. A third factor is the nature or type of fire itself. Although smoke usually accompanies fire, the amount produced can vary significantly depending upon the composition of the material that catches fire. For example oxygenated fuels such as ethyl alcohol and acetone give less smoke than the hydrocarbons from which they are derived. Thus, under free-burning conditions oxygenated fuels such as wood and polymethylmethacrylate give substantially less smoke than hydrocarbon polymers such as polyethylene and polystyrene. As a matter of fact a small number of pure fuels namely carbon monoxide, formaldehyde, metaldehyde, formic acid and methyl alcohol burn with non-luminous flames and do not produce smoke at all.

Yet another drawback of present-day ionization smoke detectors has to do with contaminating our environment. Ionization type smoke detectors use a radioactive matter ($Co^{60}$) as the source for alpha particles. Although one can argue that the amount of radioactive material currently found in each ionization smoke detector is very small (probably only tens of milligrams) the number of units in operation however easily runs into tens of millions every year. Thus, the continued usage of this type of smoke detector does pose a serious long-term liability of building up a large amount of unwanted nuclear wastes. Since the half life of $Co^{60}$ is well over 1,000 years, the potential danger should not be ignored.

Finally, there are a number of lesser issues one has to deal with when using these low-cost ionization smoke detectors. These include the trouble and cost of having to replace its battery once every year or run the risk of owning a unit that does not work because of lack of power. Also, the presently available ionization smoke detectors are rarely equipped with a visual alarm which is desirable for hearing-impaired persons.

Based upon the discussion presented above, it is clear that a rapid, reliable, low-cost, radioactive-free and maintenance free fire detector would be a most welcome addition to the imperfect world of fire detectors of today.

In U.S. Pat. No. 4,738,266, issued Apr. 19, 1988, Thatcher describes an instrument for sensing a change in the carbon dioxide concentration in ambient air. The device uses an unmodulated broadband infrared source operated at a steady temperature and a single pass band filter. In contrast, in the present invention, the temperature of the source is made to alternate between two temperatures and a dual pass band filter is used. The inclusion of the second pass band in the present invention permits the establishment of a reference signal, which renders the present invention immune to false alarms caused by factors that affect both pass bands equally, such as variations in detector sensitivity due to temperature variations, soot on the mirrors, smoke in the sample, etc. Clearly, these factors are significant for a fire detector, and the ability of the present invention to avoid confounding these factors with the carbon dioxide measurement shows the importance of the differences between the present invention and that of Thatcher.

In U.S. Pat. No. 4,648,396 issued Mar. 10, 1987, Raimer shows apparatus for monitoring the difference in carbon dioxide content between an individual's inspired and expired gas streams. The apparatus is similar to that described in the Thatcher patent, except that a feed-back loop is used to maintain the level of radiation incident on the detector constant regardless of window clouding, temperature-induced component drift, etc. The derivative of the detected signal is checked to rule out noise as a source of error in the carbon dioxide measurement.

A number of other patents show one or more features in common with the present invention, but the patents in this class all make use of moving parts (typically rotating filter wheels) or other components which are deemed to be unsuitable for use in a fire detector. These patents include: U.S. Pat. No. 4 785 184 to Bien et al.; U.S. Pat. No. 4,874,572 to Nelson, et al.; U.S. Pat. No. 4,587,427 to Talbot, et al.

The following patents employ lasers for gas analysis, in contrast to the differential temperature source and dual pass band filter used in the present invention: U.S. Pat. No. 4,535,241 to Eberhardt; U.S. Pat. No. 4,490,043 to Cramp; U.S. Pat. No. 4,489,239 to Grant, et al.; U.S. Pat. No. 3,805,074 to McCormack; U.S. Pat. No. 4,450,356 to Murray, et al.; and U.S. Pat. No. 3,998,557 to Javan.

SUMMARY OF THE INVENTION

A major purpose of the present invention is to provide a reliable and low-cost fire detector that is free from the use of radioactive material such as the alpha particle source found in present-day ionization smoke detectors. The present invention has no moving parts.

Another major purpose of the present invention is to introduce a totally new method of detecting early fires which is faster and false-alarm proof for responding to fire initiation without exceptions.

It has been known for a long time that as a process, fire can take many forms, all of which however involve chemical reaction between combustible species and oxygen from the air. In other words fire initiation is necessarily an oxidation process since it invariably involves the consumption of oxygen at the beginning. The most effective way to detect fire initiation, therefore, is to look for and detect end products of the oxidation process. With the exception of a few very specialized chemical fires (i.e., fires involving chemicals other than the commonly encountered hydrocarbons) there are three elemental entities (carbon, oxygen and hydrogen) and three compounds (carbon dioxide, carbon monoxide and water vapor) that are invariably involved in the ensuing chemical reactions or combustion of a fire.

Of the three effluent gases that are generated at the onset of a fire, carbon dioxide is the best candidate for detection by a fire detector. This is because water vapor is a very difficult gas to measure since it tends to condense easily on every available surface causing its concentration to fluctuate wildly dependent upon the environment. Carbon monoxide, on the other hand, is invariably generated in a lesser quantity than carbon dioxide, especially at the beginning of a fire. It is only when the fire temperature gets to 600° C. or above that more of it is produced at the expense of carbon dioxide and carbon. Even then more carbon dioxide is produced than carbon monoxide according to numerous studies of fire atmospheres in the past. In addition to being generated abundantly right from the start of the fire, carbon dioxide is a very stable gas. Its concentration can easily be measured accurately using Non-Dispersive Infrared (NDIR) techniques that are very advanced at the present time. The average ambient $CO_2$ concentration level of ~200 ppm (~0.02%) does not hinder the detection of additional fire-induced quantities as long as the carbon dioxide sensor is designed to have such a fine sensitivity.

Another very significant advantage of using a carbon dioxide detector rather than a smoke detector for fire initiation detection is the relative mobility of these diverse species. Smoke generation is a direct result of incomplete combustion leading to the formation of complex flammable tarry substances that, upon thermal decomposition, develop into sooty molecular clusters that consist mostly of carbon. Consequently, smoke is much heavier than carbon dioxide and therefore tends to diffuse slower in the atmosphere. Therefore, if a smoke detector and a carbon dioxide detector are located side by side some distance from a fire, the carbon dioxide detector will give the earlier alarm, primarily because of the greater mobility of the carbon dioxide gas.

Thus, a carbon dioxide detector would have definite performance advantages over the conventional smoke detector; but until the present invention, it was considered impossible to build a carbon dioxide detector that would be competitive with the smoke detector in terms of cost, sensitivity and reliability. The discussion below will demonstrate that the carbon dioxide detector of the present invention is, in fact, competitive in terms of cost, sensitivity and reliability, and superior in early warning time and freedom from false alarms.

In accordance with the present invention radiation from a quasi-blackbody source alternately operated at two distinct temperatures is conducted by a long serpentine light pipe having a uniform cross-sectional area and highly reflecting walls that serves as a gas sample chamber, to a pyroelectric detector equipped with a dual narrow bandpass infrared filter. One pass band of the filter is located at a strong absorption band of carbon dioxide (for example 4.26 microns) while the other pass band of the filter is located at a wavelength where carbon dioxide does not absorb radiation (for example, 2.20 microns).

The ratio of the detected intensities at the two temperatures is maintained constant electronically when no carbon dioxide gas is present in the sample chamber. The value of this ratio is altered by any change in the concentration of $CO_2$ gas. When both the magnitude of the ratio and its rate of change exceed preset thresholds (corresponding to a fire initiation scenerio) both audible and visual alarms will sound.

The novel features which are believed to be characteristic of the invention, both as to organization and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description only and are not intended as a definition of the lixits of the invention.

DETAILED DESCRIPTION OF THE PREFERRED EMBODIMENT

As described above, the fire detector of the present invention relies on the absorption of infrared radiation to sense the concentration of carbon dioxide in the air. The infrared radiation is generated by passing a relatively modest electric current through a resistor that is heated by the current and that emits infrared radiation as a result of this heating. By making the resistor quite small it is possible to alter its temperature at rates on the order of 100 Hz.

The resistor may be in the form of a thick film of an appropriate material, or it may consist of a metallic filament. Infrared micro-sources composed of a thick film of resistive material are available from Dynatech Electro-Optics Corporation of San Luis Obispo, California, and from Novametrix of Seattle, Washington. Micro-sources using a heated filament are available from Chicago Miniature Lamp Works of Chicago, Illinois, and from Gilway Technical Lamp Co. of Woburn, Massachusetts.

In the preferred embodiment, the radiation source is made to alternate between a higher temperature $T_2$, on the order of 500° C. and a lower temperature $T_1$ on the order of 300° C. The frequency of the alteration is on the order of 1.0 Hz.

Figure 1:
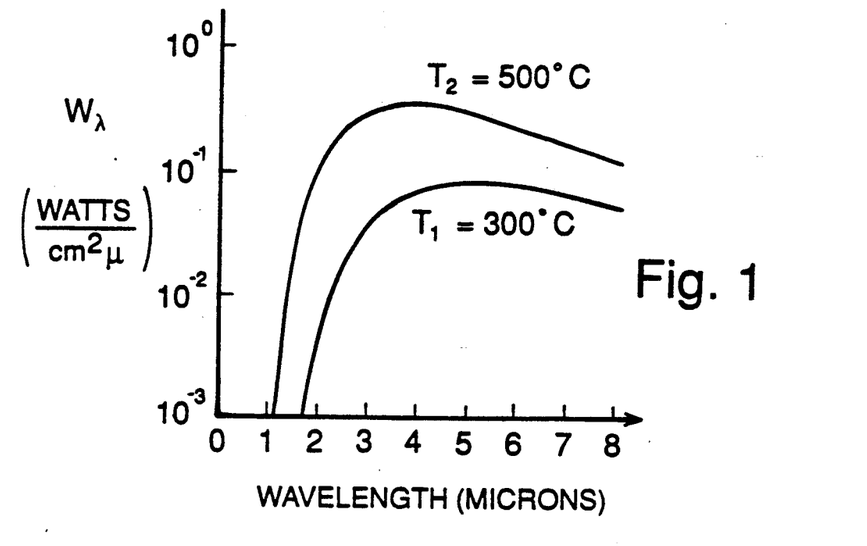
FIG. 1 is a graph showing the spectral radiant emittance versus wavelength for the differential temperature source in the preferred embodiment when operated at temperature $T_1$ and when operated at temperature $T_2$.

FIG. 1 is a graph showing the spectral radiant emittance of the source at the two temperatures, derived on the assumption that the source has an emissivity of 1.0, which is approximately true.

Only certain narrow portions of the broad spectrums shown in FIG. 1 are used in the present invention. These narrow portions are obtained by passing the radiation generated by the differential temperature source and having the spectrums shown in FIG. 1 through a dual pass band filter which absorbs all of the radiation except that which falls within two relatively narrow bands shown in FIG. 2.

Figure 2:
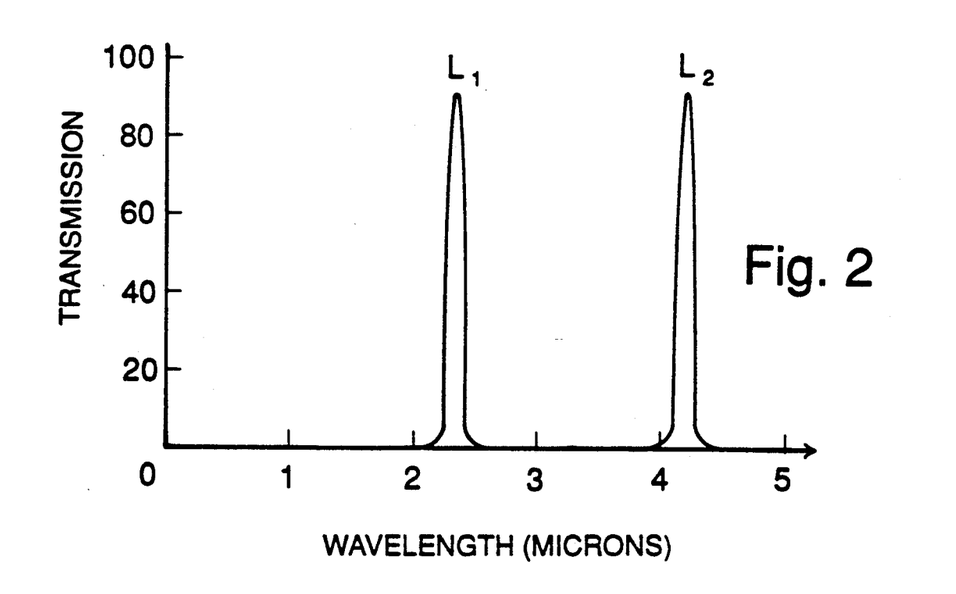
FIG. 2 is a graph showing transmission versus wavelength for the dual narrow bandpass filter used in the preferred embodiment.

In accordance with the present invention, one of these pass bands, having a wavelength L equal to 4.26 microns coincides in wavelength with a strong absorption band of carbon dioxide. The other pass band has a wavelength that is chosen to avoid the absorption bands of any of the gases present in the air. In the preferred embodiment, the wavelength $L_1$ of this pass band is approximately 2.2 microns. Such dual pass band infrared filters are available from Barr Associates of Westford, Massachusetts, and from OCLI of Santa Rosa, California.

The radiation from the differential source is passed through a sample chamber containing air that is present in a room in which fire protection is desired. Absorption by carbon dioxide will diminish the radiation received by a detector, but the diminished component will be passed by the dual band filter. Therefore, the dual band filter may be located anywhere on the optical path between the differential temperature source and the detector. Because of the temperature of the source, the dual pass band filter is located immediately in front of the detector in the preferred embodiment.

Since at any particular instant the detector is receiving both radiation at 2.20 microns and at 4.26 microns, the output of the detector can be expressed as H or L, where H and L are the signals generated by the detector when the source is pulsed at the high and low temperatures respectively. The ratio $R = H/L$ remains constant so long as the composition of the air in the sample chamber is unchanged. However, as the concentration of carbon dioxide in the sample chamber increases as a result of the influx by diffusion of carbon dioxide generated by the fire, the ratio will change in a systematic repeatable manner. The instrument can be calibrated so that the ratio can be related directly to the absolute value of the concentration of carbon dioxide in the sample chamber. However, since the purpose of the device is to provide early warning detection of a fire rather than to make absolute determinations of the carbon dioxide content, it is not necessary to calibrate the instrument extensively, but merely to adjust certain threshold levels in the presence of a known concentration of carbon dioxide.

Figure 3:
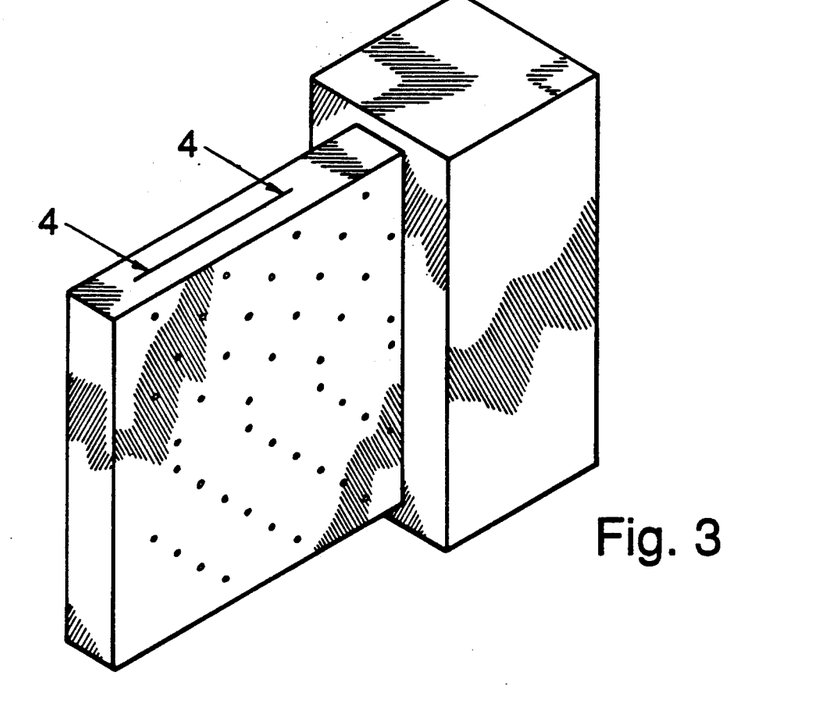
FIG. 3 is a perspective view showing a preferred embodiment of the fire detector of the present invention.
Figure 4:
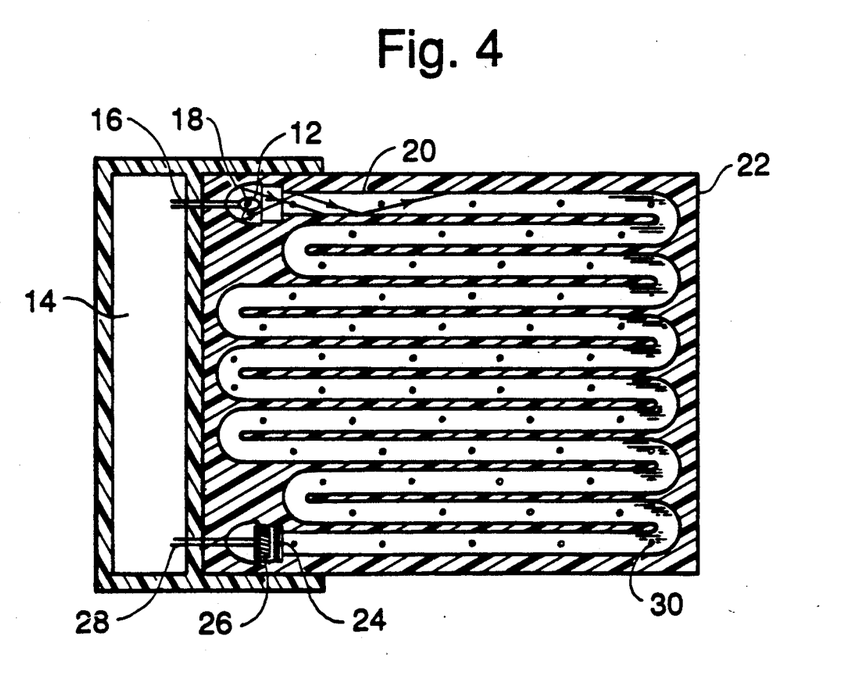
FIG. 4 is a cross sectional view in the direction 4—4 indicated in FIG. 3.

FIG. 3 shows the outward appearance of a fire detector in accordance with the present invention. FIG. 4 is a cross sectional view taken in the direction 4—4 indicated in FIG. 3. The physical arrangement of the parts is most clearly shown in FIG. 4.

The differential temperature source 12 is supplied with power by the electronic package 14 via the conductors 16. The differential temperature source is located at one focus of the ellipsoidal mirror 18 which collects a large fraction of the radiation and directs it toward the other focus of the mirror, which lies near or within the hollow serpentine light pipe 20. The light pipe 20 has the form of a passage that extends through the block 22. The walls of the light pipe 20 are highly reflective and in a preferred embodiment they are coated with a thin layer of metal by a vacuum deposition process. The radiation which has traveled the entire length of the light pipe 20 is passed through the dual pass band filter 24 and onto the detector 26 which produces a signal on the conductors 28 that represents the intensity of the radiation falling on the detector.

A number of small passages of which the passage 30 is typical permit the space within the light pipe 20 to communicate with the space adjacent the block 22. This permits carbon dioxide that is present in the air adjacent the block 22 to diffuse into the space within the light pipe 20. This diffusion takes place in less than 1 second, so that for all practical purposes, the composition of the air within the light pipe 20 is substantially the same as the composition of the air adjacent the block 22.

Figure 5:
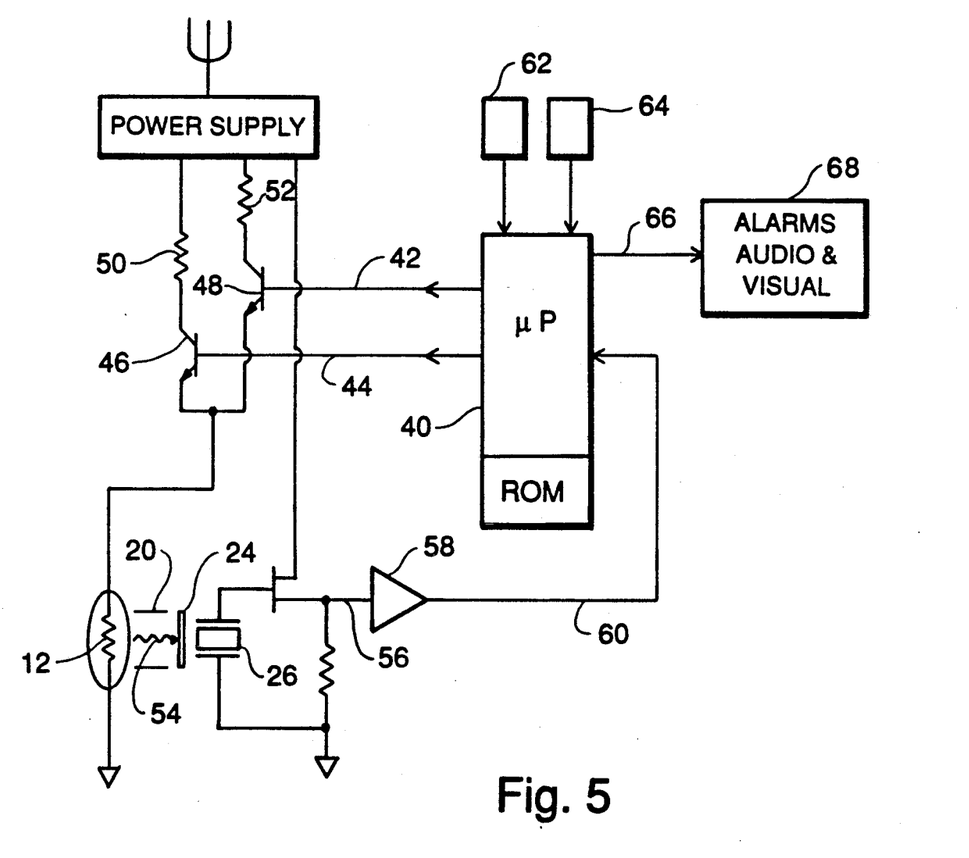
FIG. 5 is an electronic block diagram showing the electrical system in a preferred embodiment.

The serpentine shape of the light pipe 20 permits a long path length to be obtained within a block 22 of modest dimensions. For example, in the preferred embodiment, a path length of 112 cm inside a block 22 of length 10.4 cm. FIG. 5 shows the electronic system of the fire detector in a preferred embodiment. A microprocessor 40 provides timing pulses alternately on the lines 42 and 44 which are applied to the NPN transistors 46 and 48 to enable the application of a high current and a low current, respectively to the differential temperature source 12, the amount of current being determined by the resistors 50 and 52.

Radiation 54 after passing through the light pipe 20 and the dual band pass filter 24 impinges on the detector 26 which produces an electrical signal on the line 56 that is conditioned by the buffer amplifier 58 and conducted to the microprocessor 40 on the line 60. The microprocessor 40 digitizes the signal on the line 60 and determines the levels of that signal corresponding to the two temperatures $T_1$ and $T_2$ reached by the source 12. Next, the microprocessor computes the ratio of these signals, and compares the ratio with threshold levels that have been set previously by means of the potentiometers 62, 64.

In the preferred embodiment, when both the ratio and the rate of change of the ratio exceed their respective thresholds, the microprocessor produces an alarm signal on the line 66 which is used to turn on the audible and visible alarms 68. Because in the preferred embodiment both the magnitude of the ratio and its rate of change must exceed their separate thresholds before the alarm is given, there is much less chance that a false alarm will be given; however, this reduction in false alarms is bought at the expense of time, since the alarm is not given until the latter of the two events has occurred.

In an alternative embodiment, the alarm is given when either the magnitude of the ratio or its rate of change exceeds the corresponding threshold. This produces the fastest possible response, but there may be a greater number of false alarms.

In yet another alternative embodiment, the microprocessor 40 calculates a linear combination of the magnitude of the ratio and the rate of change of the ratio. The magnitude of this variable is then compared with a preset threshold, and if the threshold is exceeded, an alarm signal is generated.

Thus, there has been described a fire detector having a rapid response that results from the fact that it senses the concentration of carbon dioxide in the ambient air and also calculates the rate of buildup of the concentration of carbon dioxide. The fire detector is quite compact, its longest dimension being on the order of 10 centimeters. The fire detector of the present invention is capable of being produced at a cost of less than US $10 in quantity.

The foregoing detailed description is illustrative of one embodiment of the invention, and it is to be understood that additional embodiments thereof will be obvious to those skilled in the art. The embodiments described herein together with those additional embodiments are considered to be within the scope of the invention.

What is claimed is:

1. A fire detector having no moving parts and which senses the concentration of carbon dioxide in the ambient air, comprising in combination:

differential temperature source means including a radiating element and including means for alternating the temperature of said radiating element from $T_1$ to $T_2$ and from $T_2$ to $T_1$ while the fire detector is in use for producing radiation having a first spectrum when the temperature is $T_2$;

a sample chamber containing air and including a passage communicating with the ambient air, said sample chamber including means defining a path for the produced radiation through said sample chamber;

a dual pass band filter located in the path and having two pass bands, one of which is centered at a wavelength $L_2$ at which carbon dioxide has an absorption band and the other of which is centered at a wavelength $L_1$ at which the air in said sample chamber does not absorb radiation, for simultaneously passing radiation within the two pass bands;

detector means for intercepting radiation that has passed through said dual pass band filter and through said sample chamber and for converting the intercepted radiation to an electrical signal;

circuit means responsive to said electrical signal and to said means for alternating the temperature for determining the concentration of carbon dioxide in the air within said sample chamber and for determining the rate of change of the concentration and for producing signals representative of these quantities; and, alarm means responsive to the signals produced by said circuit means for producing an alarm in accordance with a preset criterion;

said differential temperature source means, said sample chamber, said dual pass band filter, said detector means, said circuit means and said alarm means all remaining stationary when the fire detector is in use.

2. The fire detector of claim 1 wherein said differential temperature source, said dual pass band filter and said detector means are mounted within said sample chamber.

3. The fire detector of claim 1 wherein said means defining a path further comprise a serpentine passage in a block of a rigid material, whereby the length of the serpentine passage exceeds the length of the block.

4. The fire detector of claim 1 wherein $L_2 = 4.26$ microns.

5. The fire detector of claim 4 wherein $L_1 = 2.2$ microns.

6. The fire detector of claim 1 wherein said alarm means further include means for presetting separate thresholds for the signals representative of the concentration and of the rate of change of the concentration, and wherein said alarm means produce an alarm only when both thresholds are exceeded, whereby the probability of a false alarm is reduced.

7. The fire detector of claim 1 wherein said alarm means further include means for presetting separate thresholds for the signals representative of the concentration and of the rate of change of the concentration, and wherein said alarm means produce an alarm when either threshold is exceeded, whereby an early alarm is given.

8. The fire detector of claim 1 wherein said alarm means form a linear combination of the signals representative of the concentration of carbon dioxide and of the rate of change of the concentration, and produce an alarm when the linear combination exceeds a preset threshold.

9. The fire detector of claim 1 wherein said alarm means produce an audible alarm.

10. The fire detector of claim 1 wherein said alarm means produce a visible alarm.

11. A fire detector having no moving parts and which senses the concentration of carbon dioxide in the ambient air, comprising in combination;
    differential temperature source means including a radiating element and including means for alternating the temperature of said radiating element from $T_1$ to $T_2$ and from $T_2$ to $T_1$ while the fire detector is in use for producing radiation having a first spectrum when the temperature is $T_1$ and having a second spectrum when the temperature is $T_2$;
    a sample chamber containing air and including a passage communicating with the ambient air, said sample chamber including means defining a path for the produced radiation through said sample chamber;
    a dual pass band filter located in the path and having two pass bands, one of which is centered at a wavelength $L_2$ at which carbon dioxide has an absorption band and the other of which is centered at a wavelength $L_1$ at which the air in said sample chamber does not absorb radiation, for simultaneously passing radiation within the two pass bands;
    detector means for intercepting radiation that has passed through said dual pass band filter and through said sample chamber and for converting the intercepted radiation to an electrical signal;
    circuit means responsive to said electrical signal and to said means for alternating the temperature for determining the concentration of carbon dioxide in the air within said sample chamber and for producing a signal representative of that concentration; and,
    alarm means responsive to the signal produced by said circuit means for producing an alarm in accordance with a preset criterion;
    said differential temperature source means, said sample chamber, said dual pass band filter, said detector means, said circuit means, and said alarm means all remaining stationary when the fire detector is in use.

12. The fire detector of claim 11 wherein said differential temperature source, said dual pass band filter and said detector means are mounted within said sample chamber.

13. The fire detector of claim 11 wherein said means defining a path further comprise a serpentine passage in a block of a rigid material, whereby the length of the serpentine passage exceeds the length of the block.

14. The fire detector of claim 11 wherein $L_2 = 4.26$ microns.

15. The fire detector of claim 14 wherein $L_1 = 2.2$ microns.

16. The fire detector of claim 1 wherein the preset criterion is that the signal representative of the concentration of carbon dioxide exceeds a preset threshold level.

17. The fire detector of claim 11 wherein said alarm means produce an audible alarm.

18. The fire detector of claim 11 wherein said alarm means produce a visible alarm.

19. A fire detector having no moving parts and which senses the concentration of carbon dioxide in the ambient air, comprising in combination:
    differential temperature source means including a radiating element and including means for alternating the temperature of said radiating element from $T_1$ to $T_2$ and from $T_2$ to $T_1$ while the fire detector is in use for producing radiation having a first spectrum when the temperature is $T_1$ and having a second spectrum;
    a sample chamber containing air and including a passage communicating with the ambient air, said sample chamber including means defining a path for the produced radiation through said sample chamber;
    a dual pass band filter located in the path and having two pass bands, one of which is centered at a wavelength $L_2$ at which carbon dioxide has an absorption band and the other of which is centered at a wavelength $L_1$ at which the air in said sample chamber does not absorb radiation, for simultaneously passing radiation within the two pass bands;
    detector means for intercepting radiation that has passed through said dual pass band filter and through said sample chamber and for converting the intercepted radiation to an electrical signal;
    circuit means responsive to said electrical signal and to said means for alternating the temperature for determining the rate of change of the concentration of carbon dioxide in the air within said sample chamber and for producing a signal representative of that rate; and,
    alarm means responsive to the signal produced by said circuit means for producing an alarm in accordance with a preset criterion;
    said differential temperature source, said sample chamber, said dual pass band filter, said detector means, said circuit means and said alarm means all remaining stationary when the fire detector is in use.

20. The fire detector of claim 19 wherein said differential temperature source, said dual pass band filter and said detector means are mounted within said sample chamber.

21. The fire detector of claim 19 wherein said means defining a further comprise a serpentine passage in a block of a rigid material, whereby the length of the serpentine passage exceeds the length of the block.

22. The fire detector of claim 19 where $L_2 = 4.26$ microns.

23. The fire detector of claim 22 where $L_1 = 2.2$ microns.

24. The fire detector of claim 19 wherein the preset criterion is that the signal representative of the rate of change of the concentration of carbon dioxide exceeds a preset threshold level.

25. The fire detector of claim 19 wherein said alarm means produce an audible alarm.

26. The fire detector of claim 19 wherein said alarm means produce a visible alarm.

* * * * *